United States Patent
Kobayashi et al.

(10) Patent No.: US 10,234,374 B2
(45) Date of Patent: Mar. 19, 2019

(54) METHOD FOR SELECTING BOUNDARY SAMPLE, APPARATUS FOR SELECTING BOUNDARY SAMPLE, STORAGE MEDIUM, AND SYSTEM FOR SELECTING BOUNDARY SAMPLE

(71) Applicant: Tokyo Electric Power Company Holdings, Incorporated, Tokyo (JP)

(72) Inventors: Noboru Kobayashi, Tokyo (JP); Tamotsu Ogawa, Tokyo (JP); Chikara Morooka, Tokyo (JP); Yuki Matsuoka, Tokyo (JP); Hideharu Oniki, Tokyo (JP)

(73) Assignee: Tokyo Electric Power Company Holdings, Incorporated, Tokyo (JP)

( * ) Notice: Subject to any disclaimer, the term of this patent is extended or adjusted under 35 U.S.C. 154(b) by 0 days.

(21) Appl. No.: 15/459,291

(22) Filed: Mar. 15, 2017

(65) Prior Publication Data
US 2017/0184487 A1  Jun. 29, 2017

Related U.S. Application Data

(63) Continuation-in-part of application No. PCT/JP2014/081745, filed on Dec. 1, 2014.

(51) Int. Cl.
*G01N 17/00* (2006.01)
*G01N 21/93* (2006.01)
(Continued)

(52) U.S. Cl.
CPC ........ *G01N 17/006* (2013.01); *G01M 99/004* (2013.01); *G01N 21/93* (2013.01); *G05B 23/0283* (2013.01); *G01N 2201/13* (2013.01)

(58) Field of Classification Search
CPC ... G01N 17/006; G01N 21/93; G01N 2201/13
See application file for complete search history.

(56) References Cited

U.S. PATENT DOCUMENTS

| 5,608,845 A * | 3/1997 | Ohtsuka | G07C 3/00 |
| | | | 702/34 |
| 6,226,597 B1 * | 5/2001 | Eastman | G06Q 10/06 |
| | | | 702/34 |
| 2017/0186145 A1 * | 6/2017 | Tagawa | G06T 7/001 |

FOREIGN PATENT DOCUMENTS

| JP | H09-264787 A | 10/1997 |
| JP | 2726054 B2 | 3/1998 |

(Continued)

OTHER PUBLICATIONS

X. F. Qian et al., Critical Component Life Prediction and Cost Estimation for Decision Support in Remanufacturing, 2015, IEEE, pp. 1-8, doi 978-1-4673-7929-8.*

(Continued)

*Primary Examiner* — Mischita L Henson
(74) *Attorney, Agent, or Firm* — Drinker Biddle & Reath LLP

(57) ABSTRACT

A method is used for selecting a boundary sample. The method includes acquiring a deterioration trend of a new device by performing a deterioration acceleration treatment to the new device, acquiring deterioration trends of a plurality of repaired devices which have been repaired after long-term use by performing a deterioration acceleration treatment to the plurality of repaired devices, calculating an upper limit of deterioration of the repaired device based on the deterioration trend of the new device, and selecting a boundary sample indicating a limit state in which the device can be reused as a standard of reuse of the device by specifying a repaired device having the largest deterioration among the repaired devices having a deterioration not larger than the upper limit.

4 Claims, 11 Drawing Sheets

(51) Int. Cl.
*G01M 99/00* (2011.01)
*G05B 23/02* (2006.01)

(56) References Cited

FOREIGN PATENT DOCUMENTS

| JP | 2008-64610 A | 3/2008 |
|---|---|---|
| JP | 4266864 B2 | 5/2009 |
| JP | 2010-04075 A | 1/2010 |
| JP | 4673792 B2 | 4/2011 |
| JP | 2013-161346 A | 8/2013 |

OTHER PUBLICATIONS

Hu Changhua et al., A survey on life prediction of equipment, 2015, Chinese Journal of Aeronautics, 28(1), pp. 25-33.*
International Search Report dated Feb. 24, 2015 for PCT/JP2014/081745.

* cited by examiner

FIG. 9

| | RATIO OF RUST | METHOD FOR REMOVING RUST | COATING THICKNESS | IMAGE OF RUST |
|---|---|---|---|---|
| NEW TRANSFORMER | 30.5 | — | — | — |
| No. 1 | 37.2 | B | 30 | REGISTRATION |
| No. 2 | 40.1 | B | 30 | REGISTRATION |
| No. 3 | 48.6 | A | 30 | REGISTRATION |
| No. 4 | 55.1 | C | 30 | REGISTRATION |
| No. 5 | 63.4 | C | 70 | REGISTRATION |

OK

METHOD FOR SELECTING BOUNDARY SAMPLE, APPARATUS FOR SELECTING BOUNDARY SAMPLE, STORAGE MEDIUM, AND SYSTEM FOR SELECTING BOUNDARY SAMPLE

BACKGROUND

Technical Fields

Embodiments of the present invention generally relate to a method for selecting a boundary sample, an apparatus for selecting a boundary sample, a storage medium, and a system for selecting a boundary sample.

Related Art

In related art, a device such as a transformer, a high pressure switch, or a disconnector is installed outdoors. The device includes a housing made of rubber, resin, a vinyl compound, concrete, metal, or the like. When the device is exposed to the outside air outdoors, a material of a metal housing is changed by moisture, salt, or the like. A device is deteriorated with time by the change in the material of the housing, and durability of the device is impaired.

Therefore, a treatment for preventing deterioration of the material of the housing or the like is performed in advance. For example, in order to prevent generation of rust, a rust preventive treatment is performed to a metal housing of a device. Specifically, preventive processing such as coating or plating is performed to a metal housing of a transformer, for example, refer to Japanese Unexamined Patent Application Publication No. 2010-4075.

However, a housing of a device is deteriorated due to long-term use. Here, a case in which rust is generated in a metal housing will be described, but deterioration is not limited to the rust. When coating or plating applied on a metal housing after long-term use is peeled, rust is generated at a position where peeling has occurred. A worker recovers a device in which rust has been generated and checks a state of the rust. When the amount of the rust is large and corrosion progresses, the worker discards the device. On the other hand, when the amount of the rust is small, the worker performs a rust-removing treatment or a coating treatment to reuse the device. Reuse of the device can reduce operational cost of the device.

However, a worker determines whether to discard or reuse a device. Therefore, a worker having little knowledge or experience discards a reusable device in some cases. In this case, operational cost of the device is increased.

A worker having little knowledge or experience reuses a device to be discarded in some cases. In this case, the device may be broken down in a short time, and a public disaster or power failure may occur.

SUMMARY

A method for selecting a boundary sample, may include, but is not limited to, acquiring a deterioration trend of a new device by performing a deterioration acceleration treatment to the new device, acquiring deterioration trends of a plurality of repaired devices which have been repaired after long-term use by performing a deterioration acceleration treatment to the plurality of repaired devices, calculating an upper limit of deterioration of the repaired device based on the deterioration trend of the new device, and selecting a boundary sample indicating a limit state in which the device can be reused as a standard of reuse of the device by specifying a repaired device having the largest deterioration among the repaired devices having a deterioration not larger than the upper limit.

Further features and aspects of the present disclosure will become apparent from the following detailed description of exemplary embodiments with reference to the attached drawings.

BRIEF DESCRIPTION OF THE DRAWINGS

FIG. 9 illustrates an input screen of a deterioration trend and a repairing method.

DETAILED DESCRIPTION OF THE EMBODIMENTS

Figure 1:
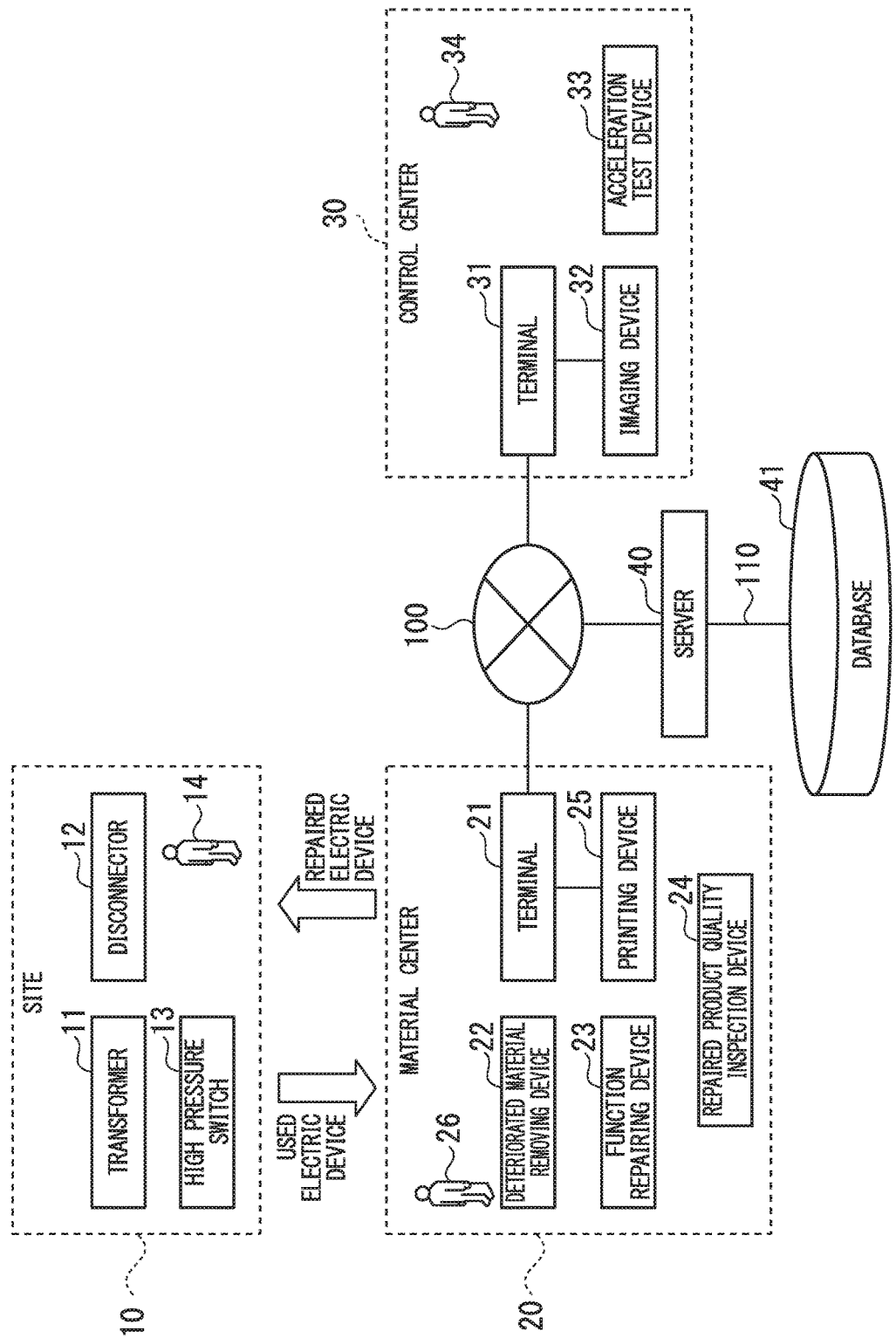
FIG. 1 is a schematic diagram illustrating a recycle system of a device.

In embodiments, a method for selecting a boundary sample may include, but is not limited to, acquiring a deterioration trend of a new device by performing a deterioration acceleration treatment to the new device; acquiring deterioration trends of a plurality of repaired devices which have been repaired after long-term use by performing a deterioration acceleration treatment to the plurality of repaired devices; calculating an upper limit of deterioration of the repaired device based on the deterioration trend of the new device; and selecting a boundary sample indicating a limit state in which the device can be reused as a standard of reuse of the device by specifying a repaired device having the largest deterioration among the repaired devices having a deterioration not larger than the upper limit.

In some cases, the selected boundary sample as a standard of reuse of the device and a repairing method corresponding to the boundary sample can be registered in a database.

In other embodiments, an apparatus for selecting a boundary sample may include, but is not limited to, a storage which stores images before repair of a plurality of repaired devices which have been repaired after long-term use; an inputter configured to allow a user to input a deterioration trend of a new device acquired by performing a deterioration acceleration treatment to the new device and deterioration trends of a plurality of repaired devices which have been repaired after long-term use, acquired by performing a deterioration acceleration treatment to the plurality of repaired devices; and a controller configured to select a boundary sample indicating a limit state in which the device can be reused as a standard of reuse of the device from images stored in the storage by calculating an upper limit of deterioration of the repaired device based on the deterioration trend of the new device input by the inputter and specifying a repaired device having the largest deterioration among the repaired devices having a deterioration not larger than the upper limit.

In some cases, the controller may be configured to display, on a display, a first input region used for inputting the deterioration trend of the new device and the deterioration trends of the plurality of repaired devices, a second input region used for inputting repairing methods which have been performed to the respective plurality of repaired devices, and a third input region used for inputting images before repair of the respective plurality of repaired devices.

In some cases, the controller may be configured to display, on the display, image data of the selected boundary sample and a repairing method corresponding to the boundary sample in response to selection of the boundary sample as a standard of reuse of the device.

In some cases, the controller may be configured to calculate an upper limit of deterioration of the repaired device based on the deterioration trend of the new device input by the inputter, specifies an image before repair of the repaired device having the largest deterioration among the plurality of repaired devices having a deterioration not larger than the upper limit from images stored in the storage, and selects the specified image before repair of the repaired device as a boundary sample indicating a limit state in which the device can be reused as a standard of reuse of the device.

In other embodiments, a system for selecting a boundary sample may include, but is not limited to, a storage medium, a server connected to the storage medium through a network, and a terminal connected to the server through the network. The terminal may include, but is not limited to, a storage which stores images before repair of a plurality of repaired devices which have been repaired after long-term use; an inputter configured to allow a user to input a deterioration trend of a new device acquired by performing a deterioration acceleration treatment to the new device and deterioration trends of a plurality of repaired devices which have been repaired after long-term use, acquired by performing a deterioration acceleration treatment to the plurality of repaired devices; and a controller configured to select a boundary sample indicating a limit state in which the device can be reused as a standard of reuse of the device from images stored in the storage by calculating an upper limit of deterioration of the repaired device based on the deterioration trend of the new device input by the inputter and specifying a repaired device having the largest deterioration among the repaired devices having a deterioration not larger than the upper limit. The server may be configured to receive image data of the boundary sample selected by the controller, and stores the image data in the storage medium.

In some cases, the controller may be configured to display, on a display, a first input region for inputting the deterioration trend of the new device and the deterioration trends of the plurality of repaired devices, a second input region for inputting repairing methods which have been performed to the respective plurality of repaired devices, and a third input region for inputting images before repair of the respective plurality of repaired devices.

In some cases, the controller may be configured to display, on the display, an image of the selected boundary sample and a repairing method corresponding to the boundary sample in response to selection of the boundary sample as a standard of reuse of the device.

In some cases, the controller may be configured to calculate an upper limit of deterioration of the repaired device based on the deterioration trend of the new device input by the inputter, to specify an image before repair of the repaired device having the largest deterioration among the plurality of repaired devices having a deterioration not larger than the upper limit from images stored in the storage, and to select the specified image before repair of the repaired device as a boundary sample indicating a limit state in which the device can be reused as a standard of reuse of the device.

In some cases, the storage medium stores image data of the boundary sample selected by the controller and repairing method data specifying a repairing method which has been performed to the repaired device specified.

In other embodiments, a non-transitory computer-readable storage medium which stores a computer program, when executed by a computer, to cause the computer to perform at least: displaying, on a display, an input screen for making a worker input images before repair of a plurality of repaired devices which have been repaired after long-term use, a deterioration trend of a new device acquired by performing a deterioration acceleration treatment to the new device, and deterioration trends of a plurality of repaired devices which have been repaired after long-term use, acquired by performing a deterioration acceleration treatment to the plurality of repaired devices; calculating an upper limit of deterioration of the repaired device based on the deterioration trend of the new device input from the input screen; selecting a boundary sample indicating a limit state in which the device can be reused as a standard of reuse of the device from images before repair of the plurality of repaired devices input from the input screen by specifying a repaired device having the largest deterioration among the repaired devices having a deterioration not larger than the upper limit; and displaying the selected boundary sample on the display.

In some cases, the device may be an electric power device.

The term "facility" used in embodiments refers to every tangible thing, which can in generally be designed, constructed, built, manufactured, installed, and maintained for performing any purpose, activities or functions in human society. In some cases, the facility may include, but is not limited to, a permanent, semi-permanent or temporary commercial or industrial property such as building, plant, or structure for performing any purpose, activities or functions in human society.

The term "event" used in embodiments refers to something that happens such as a social occasion or activity.

The term "equipment" used in embodiments refers to a set of one or more tangible articles or physical resources such as, but not limited to, some structural or tangible elements, apparatus, devices, or implements used in an operation or activity; fixed assets other than land and buildings.

The term "equipment/material" used in embodiments refers to at least one of equipment and material, for example, equipment alone, material alone or in combination.

The embodiments of the present invention will be now described herein with reference to illustrative preferred embodiments. Those skilled in the art will recognize that many alternative preferred embodiments can be accomplished using the teaching of the embodiments of the present invention and that the embodiments of the present invention is not limited to the preferred embodiments illustrated herein for explanatory purposes.

Hereinafter, a method for selecting a boundary sample, an apparatus for selecting a boundary sample, a storage medium, and a system for selecting a boundary sample according to an embodiment will be described with reference to the drawings.

First Embodiment

FIG. 1 is a schematic diagram illustrating a recycle system of a device. An electric power device such as a transformer 11, a disconnector 12, or a high pressure switch 13 is installed at a site 10 outdoors. In addition, as the electric power device, a high tension insulator, a low tension insulator, a protection pipe for an underground wire, meters, a breaker, and the like are installed. Hereinafter, an electric power device will be exemplified as a device installed outdoors. However, the present embodiment is not limited to the electric power device, but can be also applied to a device other than the electric power device, such as a gas device, a water device, or a communication device.

When an electric power device is recovered because of durability disposal, accepting a request for public disturbance, or the like, a worker 14 at the site 10 determines whether to repair and reuse the electric power device. When the worker 14 at the site 10 determines that the electric power device will be repaired and reused, the worker 14 conveys the used electric power device recovered to a material center 20. When the worker 14 at the site 10 determines that the electric power device will not be repaired and reused, the worker 14 discards the used electric power device recovered. A specific method for determining whether to repair and reuse the electric power device will be described below.

The material center 20 includes a terminal 21, a deteriorated material removing device 22, a function repairing device 23, a repaired product quality inspection device 24, and a printing device 25. A worker 26 at the material center 20 checks a state (for example, the degree of rust) of the electric power device conveyed from the site 10, and determines whether to repair and reuse the electric power device using a boundary sample described below. The boundary sample is an image indicating a limit state in which the electric power device can be reused as a standard of reuse of the electric power device. The boundary sample is printed on paper with the printing device 25. A specific method for determining whether to repair and reuse the electric power device using the boundary sample will be described below.

When the worker 26 at the material center 20 determines that the electric power device will be repaired and reused, the worker 26 repairs the recovered electric power device. The repaired electric power device is conveyed to the site 10. Thereafter, the repaired electric power device is installed and reused at the site. For example, repair of the electric power device includes a rust-removing treatment using the deteriorated material removing device 22 and a coating treatment using the function repairing device 23 and the repaired product quality inspection device 24.

A control center 30 includes a terminal 31, an imaging device 32, and an acceleration test device. A worker 34 at the control center 30 selects a boundary sample based on a result of an acceleration test with the acceleration test device 33. Specific contents of the acceleration test and a specific method for selecting a boundary sample will be described below.

A server 40 writes data on database 41, and reads data from the database 41. The database 41 is a storage medium which stores a selected boundary sample. The terminal 21 of the material center 20, the terminal 31 of the control center 30, and the server 40 are connected to a network 100. The server 40 is connected to the database 41 through a network 110. Each of the networks 100 and 110 includes any one of the Internet, a local area network (LAN), a public line, a mobile phone network, and the like.

Figure 2:
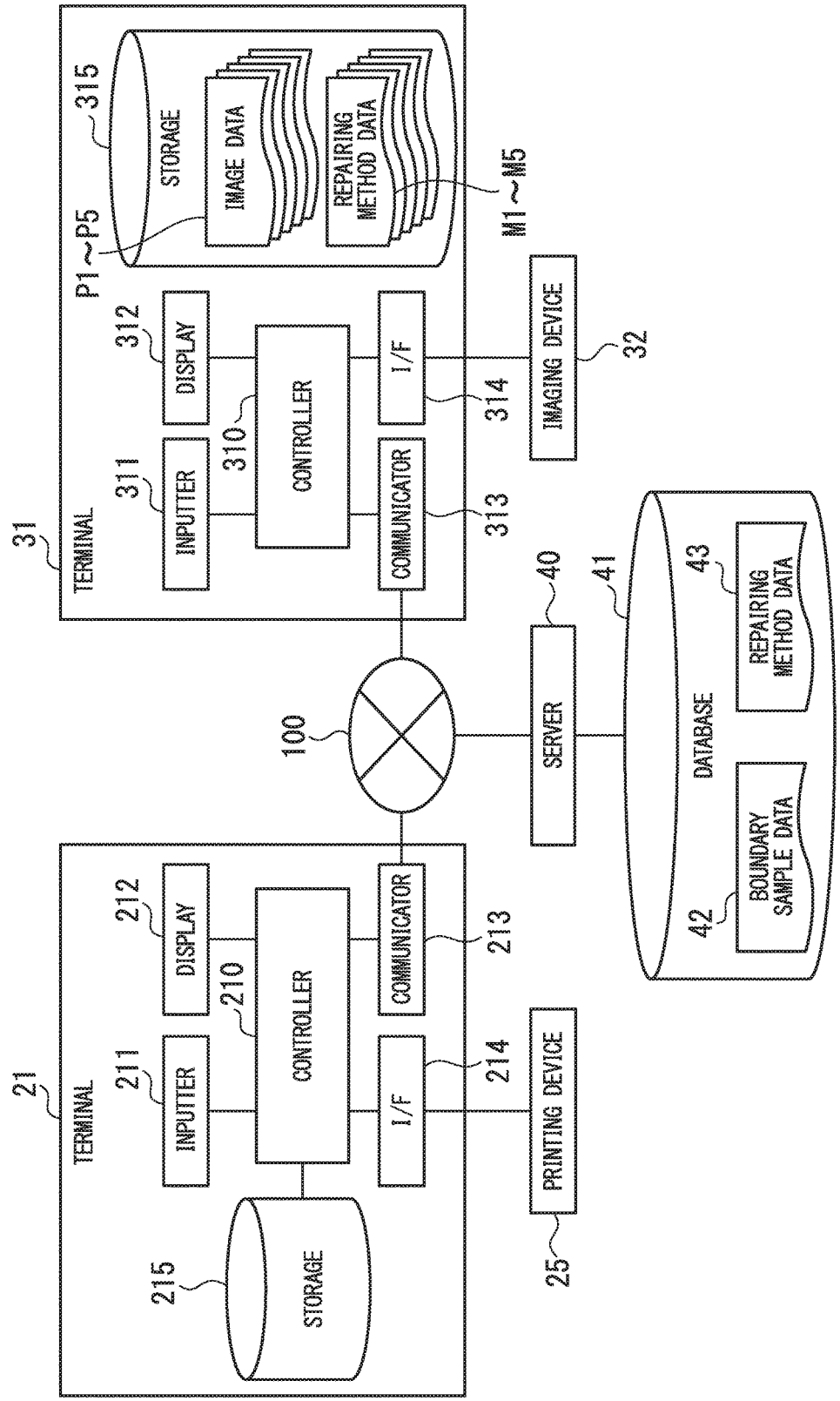
FIG. 2 is a block diagram illustrating the recycle system of the device.

FIG. 2 is a block diagram illustrating a recycle system of a device. The terminal 21 of the material center 20 is a computer including a controller 210, an inputter 211, a display 212, a communicator 213, an interface 214, and a storage 215.

The controller 210 includes a processor such as a central processing unit (CPU) and a memory which stores a program executed by the processor. The controller 210 may be a hardware such as a large scale integration (LSI) or an application specific integrated circuit (ASIC).

The inputter 211 is an input device such as a mouse or a keyboard. The display 212 is a display device such as a liquid crystal display. The communicator 213 is a communication device which transmits information to the network 100 or receives information from the network 100. The interface 214 transmits printing data to the printing device 25. The storage 215 is a storage medium such as a hard disk drive (HDD).

The terminal 31 of the control center 30 is a computer including a controller 310, an inputter 311, a display 312, a communicator 313, an interface 314, and a storage 315. The controller 310 includes a processor such as a CPU and a memory which stores a program executed by the processor. The controller 310 may be a hardware such as an LSI or an ASIC.

The inputter 311 is an input device such as a mouse or a keyboard. The display 312 is a display device such as a liquid crystal display. The communicator 313 is a communication device which transmits information to the network 100 or receives information from the network 100. The interface 314 receives image data from the imaging device 32. The storage 315 is a storage medium such as an HDD.

The server 40 is a computer which writes data on the database 41, and reads data from the database 41. The database 41 is a storage medium which stores boundary sample data 42 and repairing method data 43.

Figure 3:
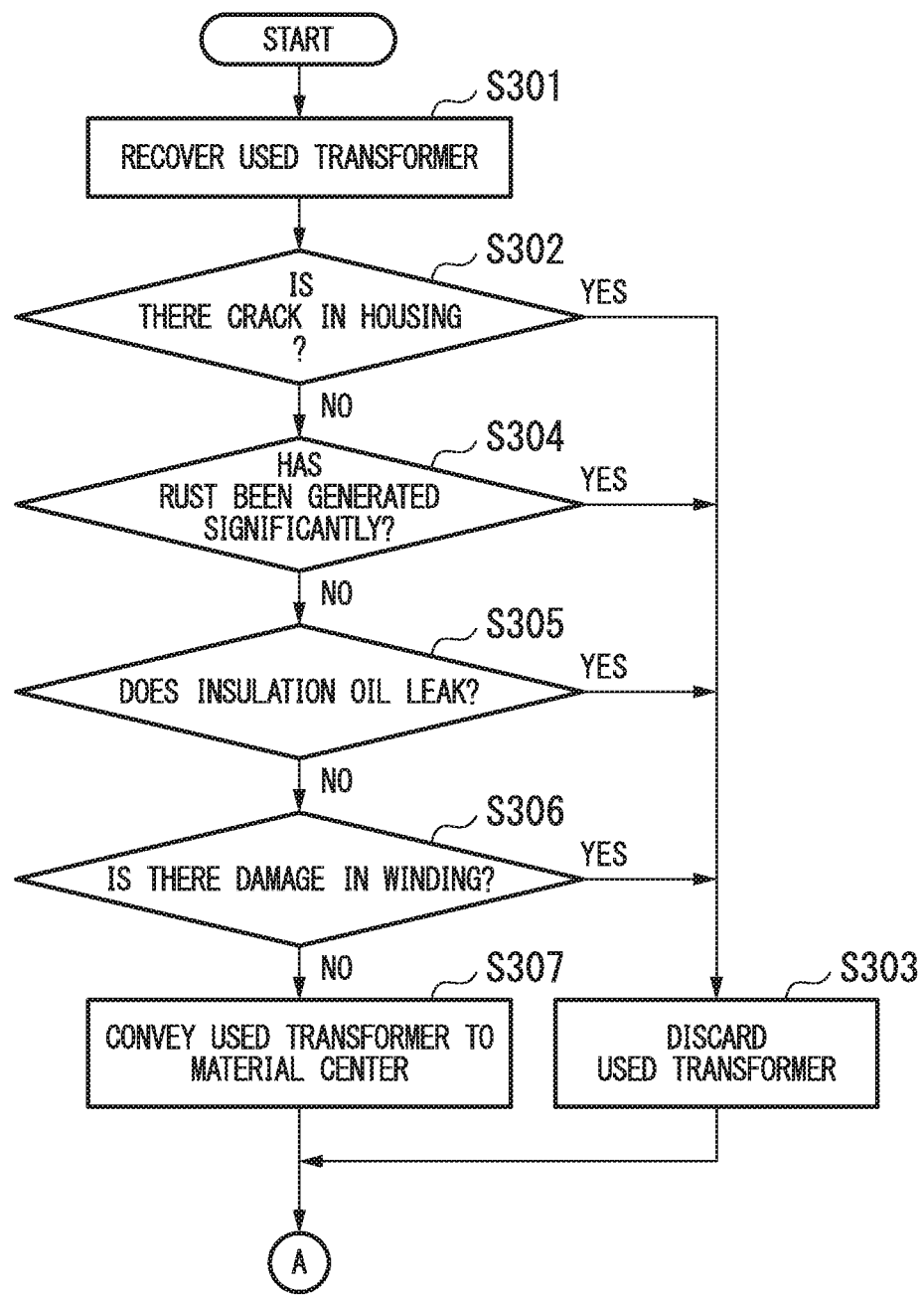
FIG. 3 is a flowchart illustrating a method for determining whether to discard a used transformer 11 by a worker 14 at a site 10.

FIG. 3 is a flowchart illustrating a method for determining whether to discard the used transformer 11 by the worker 14 at the site 10. Hereinafter, the transformer 11 will be exemplified as an electric power device, but the electric power device is not limited thereto. For example, a similar determining method is performed for another electric power device such as the disconnector 12 or the high pressure switch 13.

First, the worker 14 at the site 10 recovers the used transformer 11 which needs to be recovered (step S301). The worker 14 inspects an appearance and an inside of the used transformer 11 recovered. Then, the worker 14 determines whether there is a crack in a housing of the used transformer 11 recovered (step S302). When there is a crack in the housing of the used transformer 11 (step S302: YES), the worker 14 discards the used transformer 11 recovered (step S303).

On the other hand, when there is no crack in the housing of the used transformer 11 (step S302: NO), the worker 14 determines whether rust has been generated significantly in the housing of the used transformer 11 recovered (step S304). When rust has been generated significantly in the housing of the used transformer 11 (step S304: YES), the worker 14 discards the used transformer 11 recovered (step S303).

On the other hand, when rust has not been generated significantly in the housing of the used transformer 11 (step S304: NO), the worker 14 determines whether insulation oil leaks from the used transformer 11 recovered (step S305). When insulation oil leaks from the used transformer 11 (step S305: YES), the worker 14 discards the used transformer 11 recovered (step S303).

On the other hand, when oil does not leak from the used transformer 11 (step S305: NO), the worker 14 determines whether there is a damage in a winding in the used transformer 11 recovered (step S306). When there is a damage in the winding in the used transformer 11 (step S306: YES), the worker 14 discards the used transformer 11 recovered (step S303).

On the other hand, when there is no damage in the winding in the used transformer 11 (step S306: NO), the used transformer 11 recovered may be reused. Therefore, the worker 14 conveys the used transformer 11 recovered to the material center 20 (step S307). Thereafter, the processing shifts to a step S401 in FIG. 4.

Figure 4:
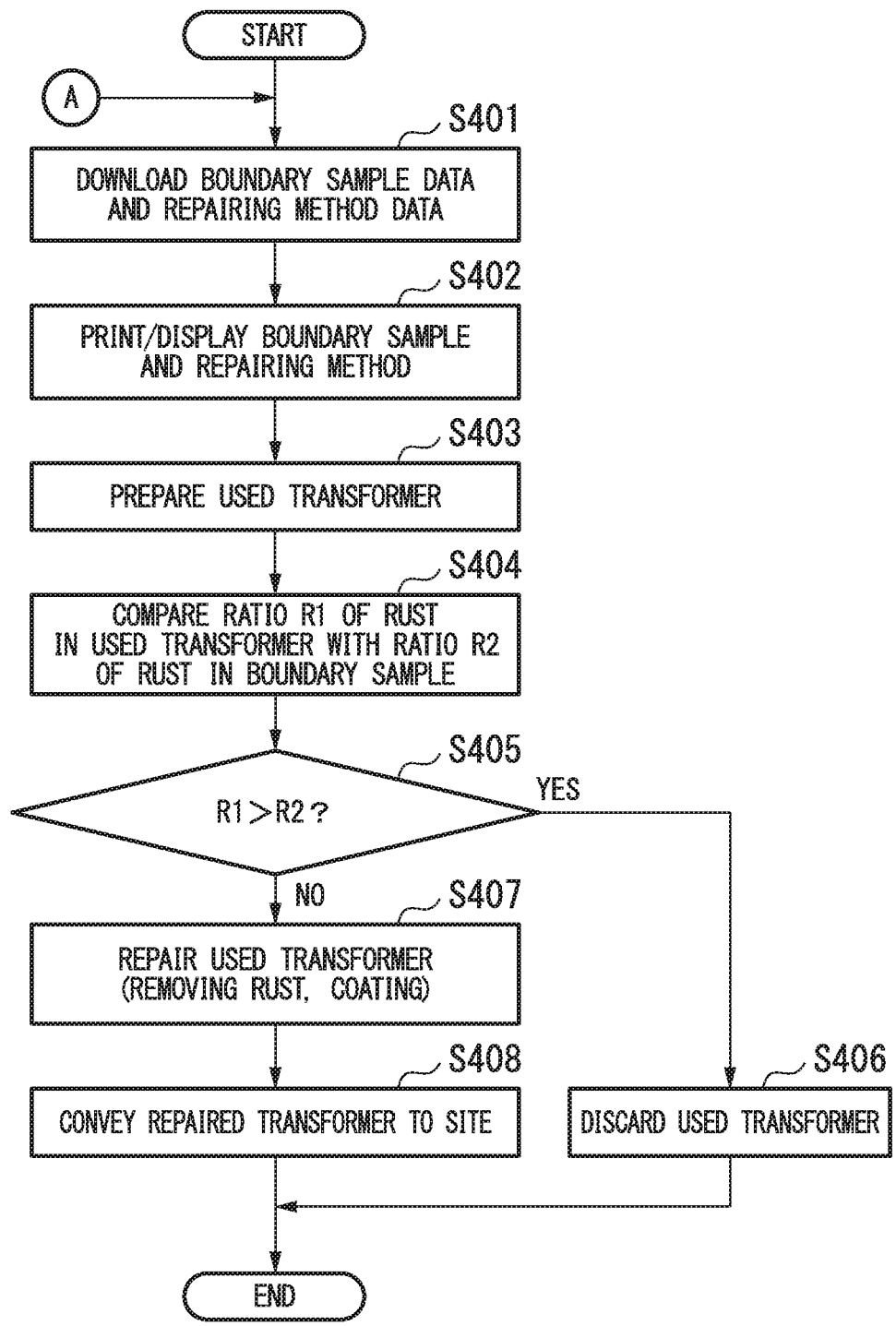
FIG. 4 is a flowchart illustrating a method for determining whether to discard the used transformer 11 by a worker 26 at a material center 20.

FIG. 4 is a flowchart illustrating a method for determining whether to discard the used transformer 11 by the worker 26 at the material center 20. This flowchart is executed in response to reception of the used transformer 11 conveyed in step S307 in FIG. 3 by the material center 20.

The worker 26 at the material center 20 inputs an instruction to download the boundary sample data 42 and the repairing method data 43 using the inputter 211 of the terminal 21 (step S401). The controller 210 transmits a request for downloading to the server 40 using a communicator in response to this instruction for downloading.

The server 40 reads the boundary sample data 42 and the repairing method data 43 from the database 41 in response to the request received from the terminal 21 The server 40 transmits the read boundary sample data 42 and repairing method data 43 to the terminal 21. The controller 210 stores the boundary sample data 42 and the repairing method data 43 received from the server 40 in the storage 215.

Subsequently, the worker 26 inputs an instruction to print the boundary sample and the repairing method using the inputter 211 of the terminal 21 (step S402). The controller 210 transmits printing databased on the boundary sample data 42 and the repairing method data 43 to the printing device 25 through the interface 214 in response to this instruction to print.

The printing device 25 prints an image of the boundary sample and the repairing method on paper in response to reception of the printing data from the terminal 21. The printing device 25 only needs to be a device which can print an image on paper, such as an inkjet printer, a laser beam printer, or a thermal printer.

An output boundary sample is an image used as a standard for determining whether to repair and reuse the used transformer 11. Specifically, the boundary sample is an image of rust on a surface of the used transformer.

The boundary sample and the repairing method may be displayed on the display 212 instead of printing the boundary sample and the repairing method using the printing device 25. The boundary sample and the repairing method may be displayed on the display 212 in addition to printing the boundary sample and the repairing method using the printing device 25. It is particularly effective to display the boundary sample and the repairing method when the display 212 is a portable display such as a tablet.

Subsequently, the worker 26 prepares the used transformer 11 received from the site 10 (step S403). The worker 26 compares a ratio R1 of rust in the used transformer 11 with a ratio R2 of rust in the boundary sample (step S404).

Here, the ratio of rust is a ratio of an area of rust with respect to a total surface area of the transformer.

Subsequently, the worker 26 determines whether the ratio R1 of rust in the used transformer 11 is larger than the ratio R2 of rust in the boundary sample (step S405). When the ratio R1 of rust in the used transformer 11 is larger than the ratio R2 of rust in the boundary sample (step S405: YES), the worker 26 discards the used transformer 11 (step S406).

On the other hand, when the ratio R1 of rust in the used transformer 11 is not larger than the ratio R2 of rust in the boundary sample (step S405: NO), the worker 26 repairs the used transformer 11 according to the printed repairing method (step S407).

For example, first, the worker 26 cleans the surface of the used transformer 11 to remove dirt. Subsequently, the worker 26 grinds rust using the deteriorated material removing device 22. Thereafter, the worker 26 performs coating in the ground range using the function repairing device 23, and checks operation using the repaired product quality inspection device 24. An amount of ground rust (rust-removing level) and a coating amount (coating thickness) are described on paper on which the repairing method is printed.

The worker 26 conveys the repaired transformer 11 to the site 10 after repairing the used transformer 11 in step S407 (step S408). The repaired transformer 11 conveyed to the site 10 is installed at the site 10 by the worker 14, and is thereby reused. In this way, operational cost of an electric power device can be reduced by not discarding but reusing the used transformer.

Figure 5:
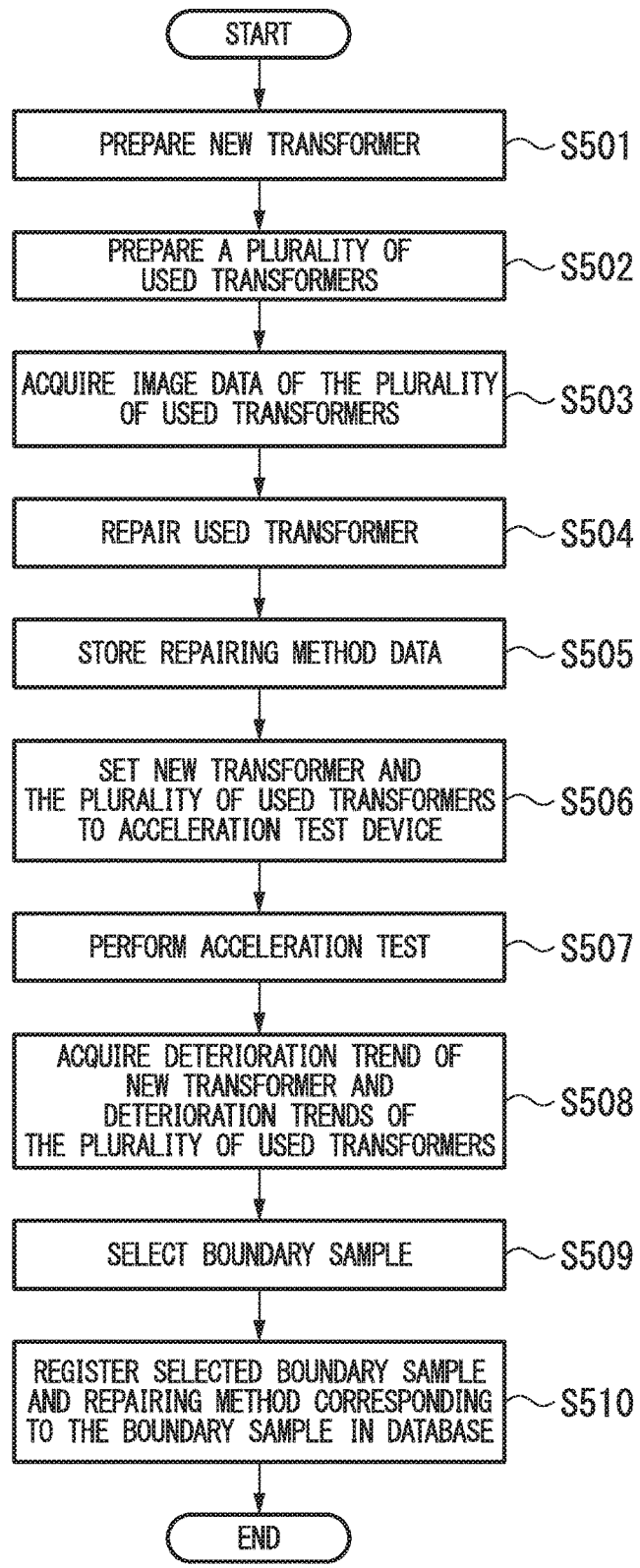
FIG. 5 is a flowchart illustrating a method for selecting a boundary sample in a first embodiment.

FIG. 5 is a flowchart illustrating a method for selecting a boundary sample in the first embodiment. This flowchart is executed by the worker 34 at the control center 30. First, the worker 34 prepares a new transformer 50 (step S501). Subsequently, the worker 34 prepares a plurality of used transformers 51 to 55 (step S502). The used transformers 51 to 55 have not been repaired yet.

In the present embodiment, five used transformers 51 to 55 are prepared for easy understanding. However, preparation of more used transformers is more preferable because more data can be acquired.

Subsequently, the worker 34 acquires image data on a surface of a housing of each of the used transformers 51 to 55 (step S503). Specifically, the worker 34 images the surface of the housing of each of the used transformers 51 to 55 using the imaging device 32. Then, the worker 34 connects the imaging device 32 to the terminal 31 of the control center 30. The controller 310 of the terminal 31 stores image data P1 to P5 imaged by the imaging device 32 in the storage 315.

Figure 6:
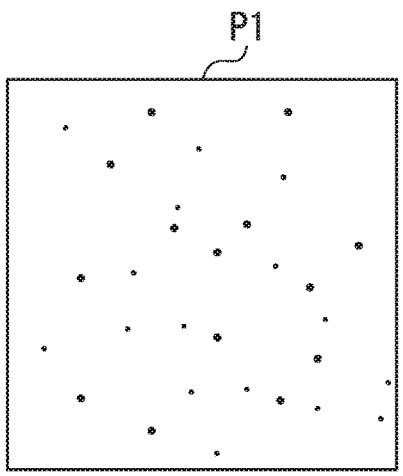
FIG. 6 illustrates an image on a surface of a housing of a used transformer.
Figure 6:
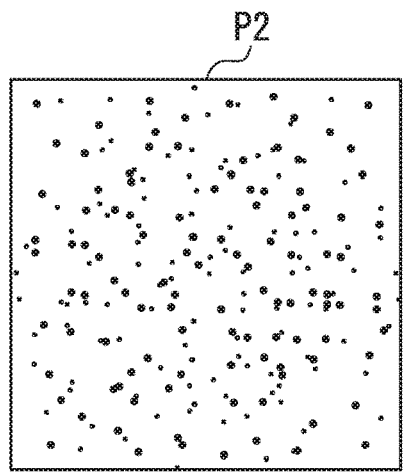
Figure 6:
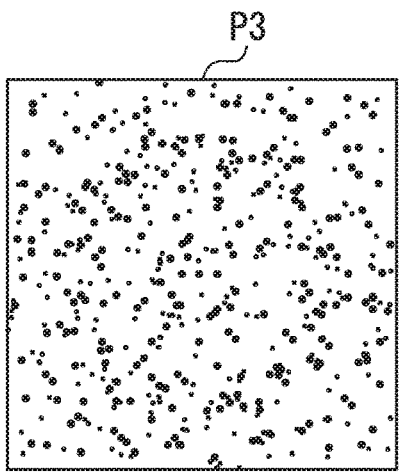
Figure 6:
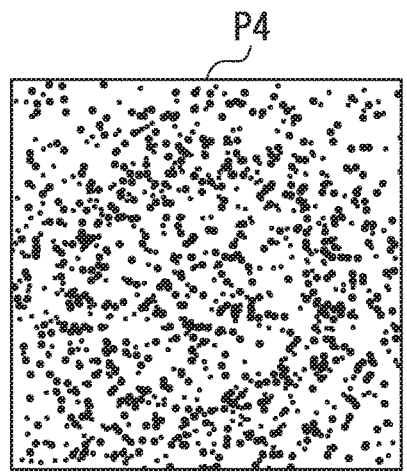
Figure 6:
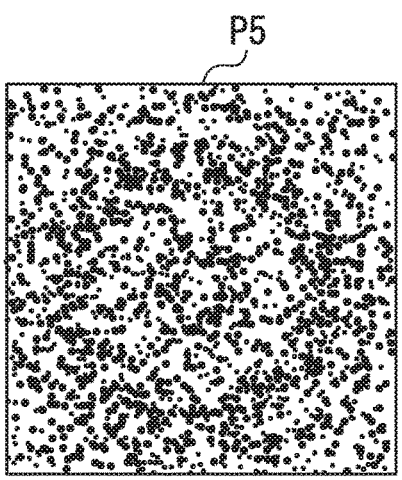

FIG. 6 illustrates an image on a surface of a housing of a used transformer. In the present embodiment, the five pieces of image data P1 to P5 obtained by imaging the used transformers 51 to 55 are stored in the storage 315. The pieces of image data P1 to P5 are images of the used transformers 51 to 55, respectively. As illustrated in FIG. 6, the ratio of rust in the used transformer 55 of the image data P5 is the largest, and the ratio of rust in the used transformer 51 of the image data P1 is the smallest.

Subsequently, the worker 34 repairs the used transformers 51 to 55 (step S504). Repaired transformers 61 to 65 are thereby obtained. As described above, the repair includes a rust-removing treatment and a coating treatment. The repaired transformers 61 to 65 correspond to the used transformers 51 to 55 repaired, respectively.

Thereafter, the worker 34 stores the repairing method performed to the used transformers 51 to 55 (for example, rust-removing level or coating thickness) in the storage 315 as repairing method data M1 to M5 (step S505).

The pieces of repairing method data M1 to M5 correspond to the used transformers 51 to 55, respectively. The pieces of repairing method data M1 to M5 correspond to the pieces of image data P1 to P5, respectively. The storage 315 stores the pieces of image data P1 to P5 by linking the pieces of image data P1 to P5 to the pieces of repairing method data M1 to M5, respectively.

Figure 7:
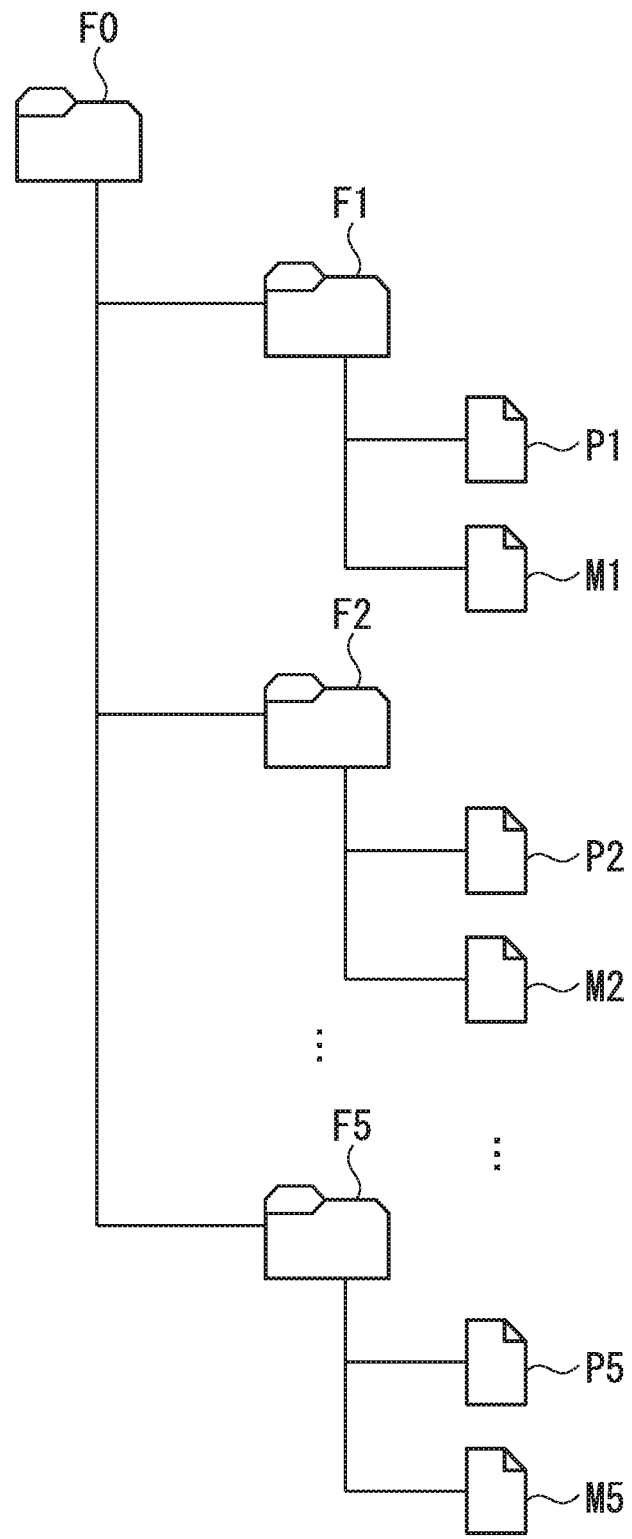
FIG. 7 illustrates a hierarchical structure of data in a storage 315.

FIG. 7 illustrates a hierarchical structure of data in the storage 315. The storage 315 includes subfolders F1 to F5 corresponding to the respective used transformers 51 to 55 in a main folder F0. The subfolders F1 to F5 are pieces of identification information corresponding to No. 1 to No. 5 in FIG. 9, respectively.

The subfolder F1 stores the image data P1 and the repairing method data M1 of the used transformer 51. The subfolder F2 stores the image data P2 and the repairing method data M2 of the used transformer 52. The subfolders F3 to F5 store the image data and the repairing method data similarly. In this way, each of the subfolders F1 to F5 includes a storage region which stores image data and a storage region which stores repairing method data.

In the present embodiment, the subfolders F1 to F5 are used as identification information of the used transformer, and the image data and the repairing method data are stored by linking the image data and the repairing method data to the identification information. However, the present invention is not limited thereto. For example, instead of organizing data using the subfolders, link information obtained by linking the identification information of the used transformer, the image data P1 to P5, and the repairing method data M1 to M5 to one another may be used.

Subsequently, the worker 34 sets the new transformer 50 and the repaired transformers 61 to 65 in the acceleration test device 33 (step S506). Thereafter, the worker 34 operates the acceleration test device 33 and performs an acceleration test (step S507). The acceleration test device 33 performs a deterioration acceleration treatment (for example, a treatment to generate rust in an accelerated manner) to the set transformer.

In the acceleration test, the acceleration test device 33 repeatedly performs three steps of a salt water spraying step, a drying step, and a wetting step. In the salt water spraying step, the acceleration test device 33 continuously sprays salt water to the new transformer 50 and the repaired transformers 61 to 65 for two hours. At this time, the temperature in the acceleration test device 33 is maintained at 35° C. For example, the spraying amount of the salt water is 1.5 [mL/h], and the concentration of the salt water is 50 [g/L].

After the salt water spraying step is finished, the acceleration test device 33 performs the drying step for four hours. In the drying step, the temperature in the acceleration test device 33 is maintained at 60° C., and the relative humidity (% rh) is maintained at less than 20 to 30%.

After the drying step is finished, the acceleration test device 33 performs the wetting step for two hours. In the wetting step, the temperature in the acceleration test device 33 is maintained at 50° C., and the humidity is maintained at 98% or more. After the wetting step is finished, the acceleration test device 33 returns to the salt water spraying step to spray salt water again.

The acceleration test device 33 repeatedly performs the salt water spraying step, the drying step, and the wetting step for 2000 hours or more. The above acceleration test generates rust in an accelerated manner in the new transformer 50 and the repaired transformers 61 to 65. The worker 34 can thereby examine deterioration trends of these transformers due to rust.

Figure 8:
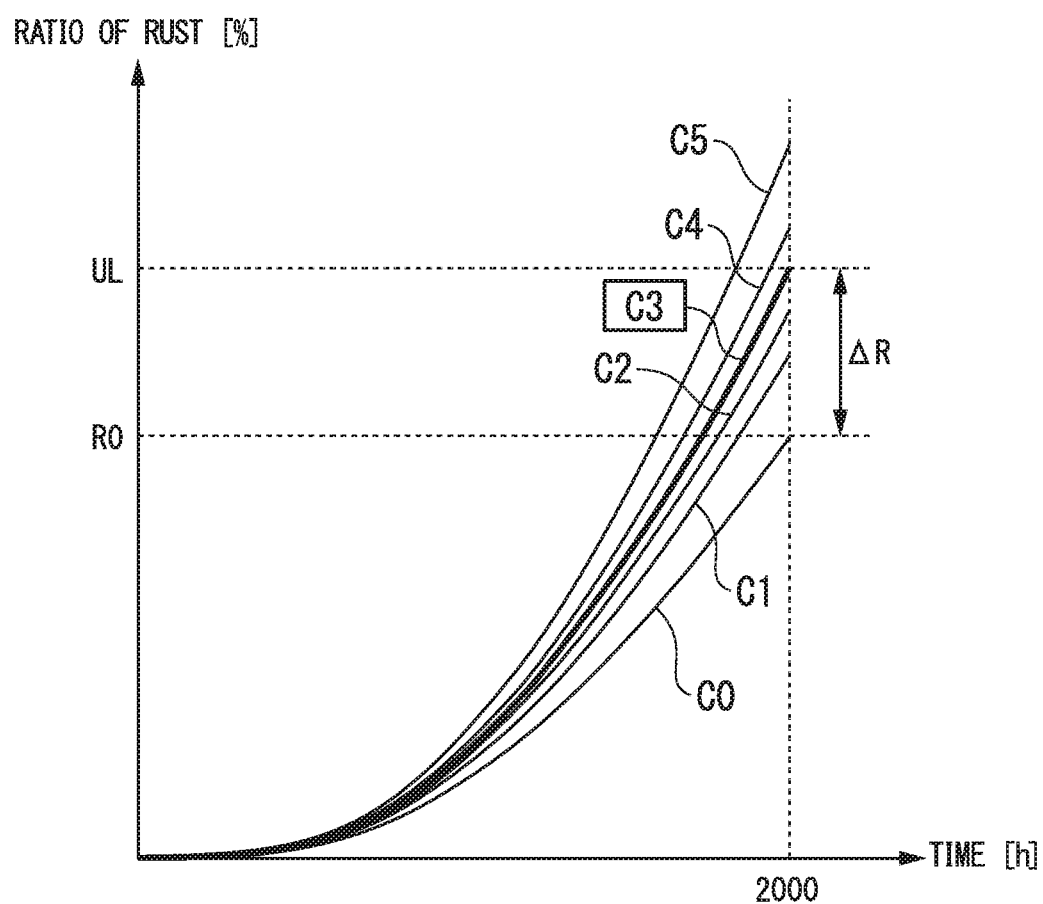
FIG. 8 illustrates a result of an acceleration test (deterioration trend of transformer).

FIG. 8 illustrates a result of the acceleration test (deterioration trend of transformer). In FIG. 8, the horizontal axis indicates elapsed time in the acceleration test, and the vertical axis indicates a ratio of rust generated in a transformer. The curve C0 indicate a change in the ratio of rust in the new transformer 50. The curves C1 to C5 indicate changes in the ratios of rust in the repaired transformers 61 to 65, respectively.

After the acceleration test is finished, the worker 34 acquires a deterioration trend of the new transformer 50 (curve C0) and deterioration trends of the repaired transformers 61 to 65 repaired after long-term use (curves C1 to C5) (step S508). The worker 34 selects a boundary sample as a standard of reuse of a used transformer by comparing the deterioration trend of the new transformer 50 with the deterioration trends of the repaired transformers 61 to 65 (step S509). Hereinafter, a method for selecting a boundary sample will be described specifically.

As illustrated in FIG. 8, when the acceleration test is finished, the ratio of rust in the new transformer 50 has increased to R0. When the acceleration test is finished, if a ratio of rust in a repaired transformer is equal to R0, it can be said that durability of this repaired transformer with respect to rust is almost equal to that of a new transformer.

Therefore, in the present embodiment, a repaired transformer having a ratio of rust (deterioration trend) of less than the upper limit UL is assumed to be a repaired transformer reusable. Here, UL=R0+ΔR ΔR is a value appropriately set considering cost for repair, durability of a repaired transformer, and the like totally. For example, ΔR may be 10[%].

First, the worker 34 extracts a repaired transformer having a ratio of rust of less than the upper limit UL. The examples illustrated in FIG. 8 indicate that values of the curves C1 to C3 are less than the upper limit UL when the acceleration test is finished. Therefore, the worker 34 extracts the repaired transformers 61 to 63.

Subsequently, the worker 34 specifies a repaired transformer having the largest ratio of rust among the repaired transformers 61 to 63 extracted. In the examples illustrated in FIG. 8, the ratio of rust of the curve C3 is the largest among the curves C1 to C3. Therefore, the worker 34 specifies the repaired transformer 63 corresponding to the curve C3.

Subsequently, the worker 34 selects the image data P3 before repair of the repaired transformer 63 specified as a boundary sample. Specifically, the controller 310 of the terminal 31 displays the image data P1 to P5 illustrated in FIG. 6 as a candidate for a boundary sample on the display 312. The worker 34 inputs an instruction to select the image data P3 as a boundary sample using the inputter 311 of the terminal 31.

The controller 310 reads the selected image data P3 from the storage 315 in response to the instruction to select a boundary sample. Then, the controller 310 reads the repairing method data M3 corresponding to the image data P3 from the storage 315. Thereafter, the controller 310 transmits the read image data P3 and repairing method data M3 to the server 40 using the communicator 313.

The server 40 stores the image data P3 received from the terminal 31 in the database 41 as the boundary sample data 42. The server 40 stores the repairing method data M3 received from the terminal 31 in the database 41 as the repairing method data 43. Registration of the boundary sample data 42 and the repairing method data 43 into the database 41 is completed by the above processing (step S510).

The repairing method data 43 includes data on a rust-removing level and data on a coating thickness. The rust-removing level includes three levels of A, B, and C. The rust-removing level A is a level at which rust is ground until base metal is exposed and the rust is removed completely. The rust-removing level B is a level at which rust is ground until rust remains slightly. The rust-removing level C is a level at which rust is not removed at all.

In the case of the rust-removing level A, rust can be removed completely, but a plated layer for preventing rust on a surface of a transformer is broken by grinding rust until base metal is exposed. On the contrary, in the case of the rust-removing level C, a plated layer is not broken, but much rust remains. Therefore, a suitable rust-removing level is preferably selected according to a state of rust.

The coating thickness is set to 10 [μm] to 90 [μm]. When the coating thickness is too small, coating is peeled easily. On the contrary, when the coating thickness is too large, coating bulges partially and is broken. Therefore, a suitable coating thickness is preferably selected according to a state of rust.

In step S407 in FIG. 4, the worker 26 at the material center 20 prints the repairing method data 43 (for example, rust-removing level: B, coating thickness: 35 [μm]) registered in the database 41 on paper using the printing device 25, and checks the data. Then, the worker 26 repairs a used transformer according to the printed repairing method. This makes it possible to reuse a used transformer normally discarded and to further reduce operational cost of an electric power device.

Second Embodiment

Next, a second embodiment will be described. In the first embodiment, the worker 34 at the control center 30 selects a boundary sample. However, in the second embodiment, a terminal 31 at a control center 30 selects a boundary sample automatically. Hereinafter, the second embodiment will be described in detail.

FIG. 9 illustrates an input screen of a deterioration trend and a repairing method. A worker 34 at the control center 30 gives an instruction to display an input screen 90 using an inputter 311 of the terminal 31. A controller 310 of the terminal 31 displays the input screen 90 on a display 312 in response to the instruction to display the input screen 90.

The worker 34 moves a pointer 91 on the input screen 90 by operating a mouse included in the inputter 311. The worker 34 inputs deterioration trend input regions 92a to 92f, and repairing method input regions 93b to 93f and 94b to 94f using a keyboard included in the inputter 311. In the present embodiment, the deterioration trend is assumed to be a ratio of rust, and the repairing method is assumed to be a rust-removing method and a coating thickness.

Rust image registration keys 95b to 95f are keys for registering an image of rust of a used transformer before repair. The worker 34 clicks the rust image registration keys 95b to 95f by operating the mouse included in the inputter 311, and registers an image before repair of each of No. 1 to 5 repaired transformers. When the above input is completed, the worker 34 clicks an Ok key 96.

The controller 310 of the terminal 31 selects a boundary sample and a repairing method in response to clicking of the Ok key 96. A specific method for selecting a boundary sample and a repairing method will be described below.

When the controller 310 selects a boundary sample and a repairing method, the controller 310 transmits the selected boundary sample and repairing method to the server 40. The transmitted boundary sample and repairing method are registered in a database 41.

Figure 10:
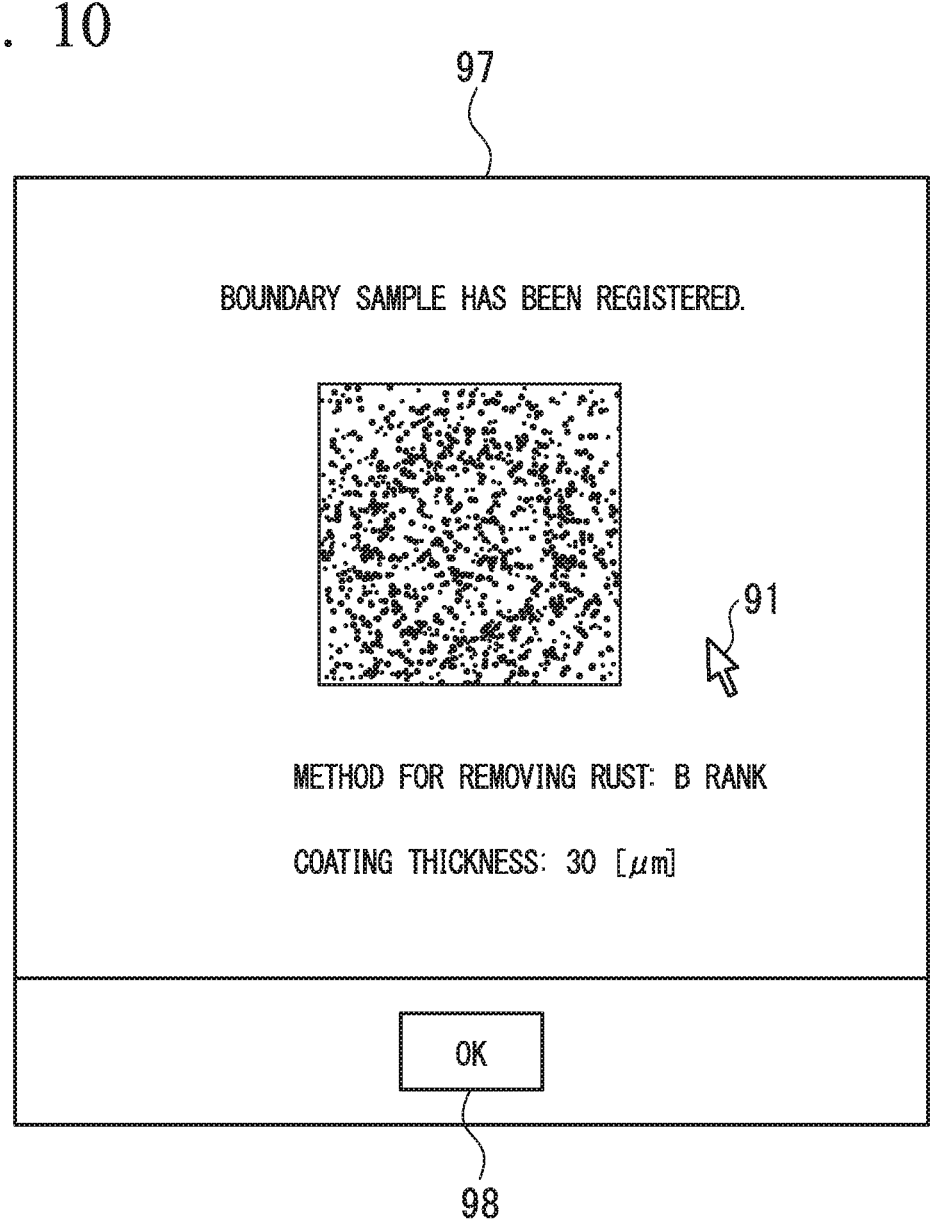
FIG. 10 illustrates a screen indicating a registration result of a boundary sample and a repairing method.

FIG. 10 illustrates a registration result of a boundary sample and a repairing method. When the boundary sample and the repairing method are registered in the database 41, the controller 310 displays a registration completion screen 97 illustrated in FIG. 10 on the display 312. As illustrated in FIG. 10, an image of the boundary sample and the repairing method (rust-removing method: B rank, coating thickness: 35 [μm]) are displayed. When the worker 34 clicks an Ok key 98, the screen in FIG. 10 is closed.

Figure 11:
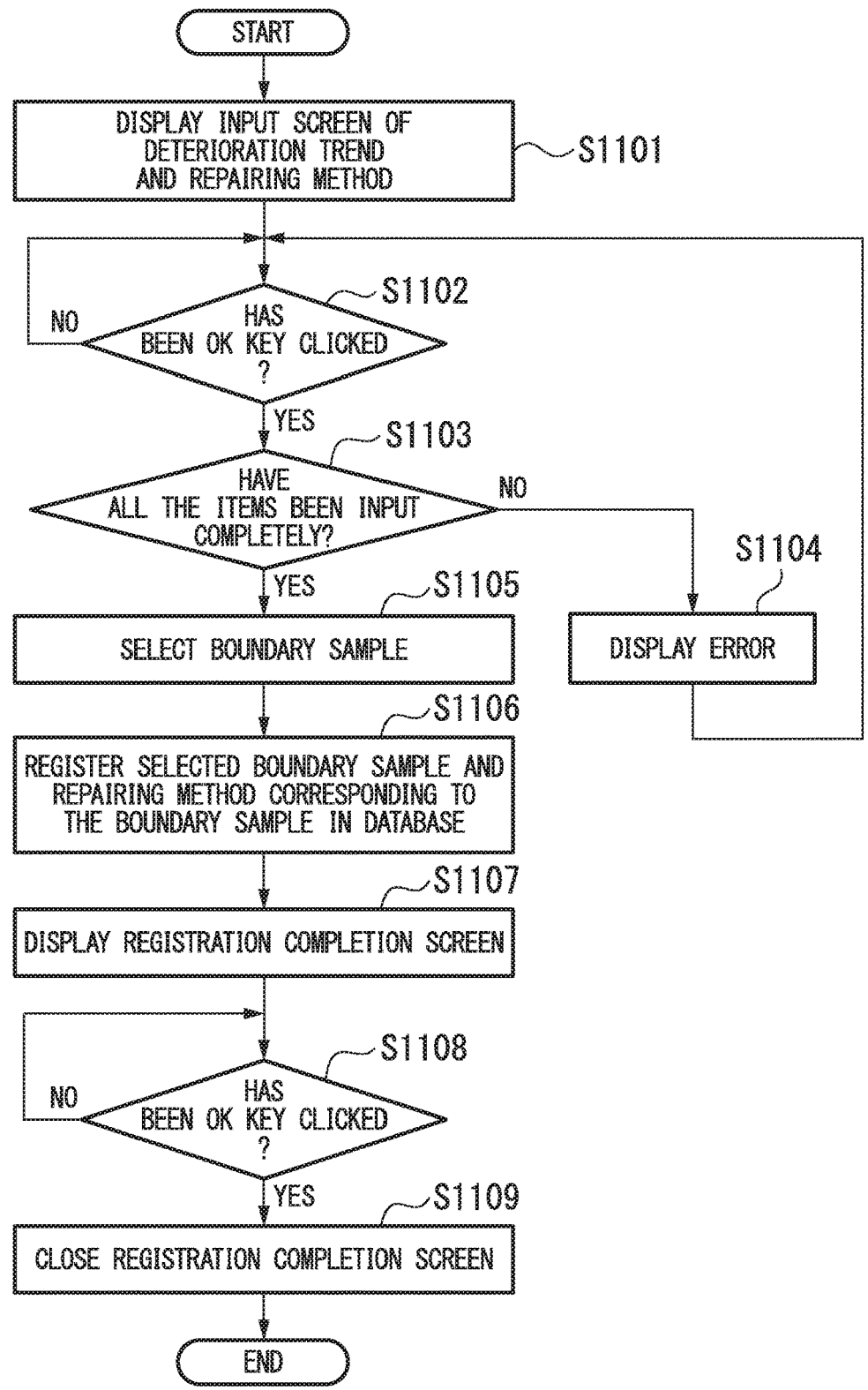
FIG. 11 is a flowchart illustrating a method for selecting a boundary sample in a second embodiment.

FIG. 11 is a flowchart illustrating a method for selecting a boundary sample in the second embodiment. Processing in accordance with this flowchart is executed by the controller 310 of the terminal 31. A program to execute this flowchart is stored in a storage 315.

First, as illustrated in FIG. 9, the controller 310 of the terminal 31 displays the input screen 90 of the deterioration trend and the repairing method on the display 312 (step S1101). Subsequently, the controller 310 waits until the Ok key 96 is clicked (step S1102).

When the Ok key 96 is clicked (step S1102: YES), the controller 310 determines whether all the items of the input screen 90 (ratio of rust, rust-removing method, coating thickness, and image before repair (rust image)) have been input (step S1103). When all the items have not been input (step S1103: NO), the controller 310 displays an error message that an item has not been input yet (step S1104), and returns to processing in step S1102.

On the other hand, when all the items have been input (step S1103: YES), the controller 310 selects a boundary sample (step S1105). Specifically, the controller 310 calculates the upper limit UL illustrated in FIG. 8 based on a deterioration trend (ratio of rust) R0 of a new transformer input into the deterioration trend input region 92a. Here, UL=R0+ΔR as described above, ΔR is set to 10[%]. In the case of an example illustrated in FIG. 9, UL=30.5+10=40.5 [%].

Subsequently, the controller 310 extracts a repaired transformer having a deterioration trend (ratio of rust) of the upper limit UL or less. In the example illustrated in FIG. 9, the controller 310 extracts No. 1 repaired transformer (37.2 [%]) and No. 2 repaired transformer (40.1[%]) having deterioration trends of the upper limit UL=40.5[%] or less.

Subsequently, the controller 310 specifies a repaired transformer having the largest deterioration trend (ratio of rust) of the No. 1 and No. 2 repaired transformers extracted. In the example illustrated in FIG. 9, the ratio of rust of the No. 2 repaired transformer (40.1[%]) is larger than that of the No. 1 repaired transformer (37.2[%]). Therefore, the controller 310 selects an image before repair of the No. 2 repaired transformer as a boundary sample.

Subsequently, the controller 310 transmits the selected boundary sample and a repairing method corresponding to the boundary sample (rust-removing method: B rank, coating thickness: 35 [μm]) to the server 40. The selected boundary sample and the repairing method are registered in the database 41 (step S1106). Thereafter, the controller 310 displays the registration completion screen 97 illustrated in FIG. 10 on the display 312 (step S1107).

Subsequently, the controller 310 waits until the Ok key 98 in FIG. 10 is clicked (step S1108). When the Ok key 98 is clicked (step S1108: YES), the controller 310 closes the registration completion screen 97 (step S1109).

The input processing in FIG. 9 may be executed only by some authorized workers. For example, a worker is authenticated by an ID or a password, and inputting by a worker other than the authorized workers may be prevented.

As described above, according to the second embodiment, a worker 26 at a material center 20 can use a boundary sample registered in the database 41. Even a worker having little knowledge or experience can thereby properly determine whether to discard or reuse an electric power device (transformer or the like).

According to the second embodiment, the worker 34 at the control center 30 does not need to select a boundary sample or a repairing method, and therefore workload of the worker 34 can be reduced.

The electric power device has been exemplified as a device installed outdoors. However, the present embodiment is not limited to the electric power device but can be also applied to a device other than the electric power device, such as a gas device, a water device, or a communication device. The transformer has been exemplified as an electric power device, but the electric power device is not limited thereto. For example, the method for selecting a boundary sample according to the present embodiment may be applied to an electric power device such as a disconnector, a high pressure switch, a high tension insulator, a low tension insulator, a protection pipe for an underground wire, meters, or a breaker.

As described above, the worker 34 or the terminal 31 acquires a deterioration trend of a new device and a deterioration trend of a repaired device. The worker 34 or the terminal 31 selects a boundary sample indicating a limit state in which a device can be reused as a standard of reuse of the device by comparing the deterioration trend of the new device with the deterioration trend of the repaired device. Even the worker 26 at the material center 20 having little knowledge or experience can thereby properly determine whether to discard or reuse a used device.

The apparatus, systems and methods in the above-described embodiments may be deployed in part or in whole through machines, a system of circuits, circuitry, hardware processors that executes computer software, software components, program codes, and/or instructions on one or more machines, a system of circuits, circuitry, hardware processors. In some cases, the one or more machines, a system of circuits, circuitry, hardware processors may be part of a general-purpose computer, a server, a cloud server, a client, network infrastructure, mobile computing platform, stationary computing platform, or other computing platform. One or more processors may be any kind of computational or processing device or devices which are capable of executing program instructions, codes, binary instructions and the like. The one or more hardware processors may be or include a signal processor, digital processor, embedded processor, microprocessor or any variants such as a co-processor, for example, math co-processor, graphic co-processor, communication co-processor and the like that may directly or indirectly facilitate execution of program codes or program instructions stored thereon.

In addition, the one or more hardware processors may enable execution of multiple programs, threads, and codes. The threads may be executed simultaneously to enhance the performance of the one or more hardware processors and to facilitate simultaneous operations of the application. Program codes, program instructions and the like described herein may be implemented in one or more threads. The one or more hardware processors may include memory that stores codes, instructions and programs as described herein.

The machines, a system of circuits, circuitry, hardware processors may access a non-transitory processor-readable storage medium through an interface that may store codes, instructions and programs as described herein and elsewhere. The non-transitory processor-readable storage medium associated with the machines, a system of circuits, circuitry, hardware processors for storing programs, codes, program instructions or other type of instructions capable of being executed by the computing or processing device may include but may not be limited to one or more of a memory, hard disk, flash drive, RAM, ROM, CD-ROM, DVD, cache and the like.

A processor may include one or more cores that may enhance speed and performance of a multiprocessor. In some embodiments, the process may be a dual core processor, quad core processors, other chip-level multiprocessor and the like that combine two or more independent cores.

The methods, apparatus and systems described herein may be deployed in part or in whole through a machine that executes computer software on a server, client, firewall, gateway, hub, router, or other such computer and/or networking hardware.

The software program may be associated with one or more client that may include a file client, print client, domain client, internet client, intranet client and other variants such as secondary client, host client, distributed client and the like. The client may include one or more of memories, processors, computer readable media, storage media, physical and virtual ports, communication devices, and interfaces capable of accessing other clients, servers, machines, and devices through a wired or a wireless medium, and the like. The programs or codes as described herein may be executed by the client. In addition, other devices required for execution of methods as described in this application may be considered as a part of the infrastructure associated with the client. The client may provide an interface to other devices including servers, other clients, printers, database servers, print servers, file servers, communication servers, distributed servers and the like. This coupling and/or connection may facilitate remote execution of program across the network. The networking of some or all of these devices may facilitate parallel processing of a program or method at one or more location. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The software program may be associated with one or more servers that may include a file server, print server, domain server, internet server, intranet server and other variants such as secondary server, host server, distributed server and the like. The server may include one or more of memories, processors, computer readable media, storage media, physical and virtual ports, communication devices, and interfaces capable of accessing other servers, clients, machines, and devices through a wired or a wireless medium, and the like. The methods, programs or codes as described herein may be executed by the server. In addition, other devices required for execution of methods as described in this application may be considered as a part of the infrastructure associated with the server. The server may provide an interface to other devices including clients, other servers, printers, database servers, print servers, file servers, communication servers, distributed servers, social networks, and the like. This coupling and/or connection may facilitate remote execution of program across the network. The networking of some or all of these devices may facilitate parallel processing of a program or method at one or more locations. Any of the devices attached to the server through an interface may include at least one storage medium capable of storing programs, codes and/or instructions. A central repository may provide program instructions to be executed on different devices. In this implementation, the remote repository may act as a storage medium for program codes, instructions, and programs.

The methods, apparatus and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing devices associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory, for example, USB sticks or keys, floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The modules, engines, components, and elements described herein, including in flow charts and block diagrams throughout the figures, imply logical boundaries between the modules, engines, components, and elements. However, according to software or hardware engineering practices, the modules, engines, components, and elements and the functions thereof may be implemented on one or more processors, computers, machines through computer executable media, which are capable of executing program instructions stored thereon as a monolithic software structure, as standalone software modules, or as modules that employ external routines, codes, services, or any combination of these, and all such implementations may be within the scope of the present disclosure. Examples of such machines may include, but is not limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers, processor-embedded eyewear and the like. Furthermore, the modules, engines, components, and elements in the flow chart and block diagrams or any other logical component may be implemented on one or more machines, computers or processors capable of executing program instructions. Whereas the foregoing descriptions and drawings to which the descriptions have been referred set forth some functional aspects of the disclosed systems, no particular arrangement of software for implementing these functional aspects should be inferred from these descriptions unless explicitly stated or otherwise clear from the context. It will also be appreciated that the various steps identified and described above may be varied, and that the order of steps may be adapted to particular applications of the techniques disclosed herein. All such variations and modifications are intended to fall within the scope of this disclosure. The descriptions of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

As used herein, the following directional terms "front, back, above, downward, right, left, vertical, horizontal, below, transverse, row and column" as well as any other similar directional terms refer to those instructions of a device equipped with embodiments of the present invention. Accordingly, these terms, as utilized to describe embodiments of the present invention should be interpreted relative to a device equipped with embodiments of the present invention.

Each element for the system, device and apparatus described above can be implemented by hardware with or without software. In some cases, the system, device and apparatus may be implemented by one or more hardware processors and one or more software components wherein the one or more software components are to be executed by the one or more hardware processors to implement each element for the system, device and apparatus. In some other cases, the system, device and apparatus may be implemented by a system of circuits or circuitry configured to perform each operation of each element for the system, device and apparatus.

While the present disclosure includes many embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A method for selecting a boundary sample, the method comprising:
    preparing a plurality of devices that are new and have not been used;
    placing the plurality of devices in long-term use outdoors without performing any deterioration acceleration treatment to the plurality of devices;
    acquiring respective first deterioration trends of the plurality of devices that have not been repaired after the plurality of devices have been placed in long-term use outdoors without performing any deterioration acceleration treatment to the plurality of devices;
    repairing the plurality of devices after the plurality of devices have been placed in long-term use outdoors without performing any deterioration acceleration treatment to the plurality of devices;
    acquiring respective second deterioration trends of the plurality of devices that have been repaired;
    calculating an upper limit of deterioration for repaired devices after long-term use outdoors based on the respective first deterioration trends of the plurality of devices that have not been repaired and based on a predetermined value;
    specifying a device repaired having a largest deterioration trend from among the respective second deterioration trends of the plurality of devices repaired, wherein the respective second deterioration trends of the plurality of devices repaired are not larger in deterioration than the calculated upper limit of deterioration; and
    selecting a device, which corresponds to the device repaired and specified, as a boundary sample device indicating a limit state in which the device can be reused as a standard of reuse of the device.

2. The method according to claim 1, wherein the selected boundary sample device as the standard of reuse of the device and a repairing method corresponding to the boundary sample device are registered in a database.

3. The method according to claim 1, wherein the predetermined value is based on at least one of a cost of repair for the device and a durability of the device after repair.

4. The method according to claim 1, wherein the devices include one or more of an electrical transformer, an electrical disconnector, a high pressure electrical switch, a high tension insulator, a low tension insulator, a protection pipe for an underground wire, an electrical meter, and an electrical breaker.

* * * * *